United States Patent [19]

Davis

[11] Patent Number: 4,640,895
[45] Date of Patent: Feb. 3, 1987

[54] BIPHASIC MEDIA CULTURE APPARATUS

[75] Inventor: Sherman G. Davis, Shaker Heights, Ohio

[73] Assignee: Gibco Division, the Mogul Corporation, Chagrin Falls, Ohio

[21] Appl. No.: 432,848

[22] Filed: Oct. 15, 1982

[51] Int. Cl.$^4$ .............. C12M 1/24; C12M 1/18; C12M 1/26; B65D 1/04
[52] U.S. Cl. .................. 435/296; 435/300; 435/292; 248/146; 248/311.2; 215/6
[58] Field of Search ............... 215/6, 100 R; 435/296, 435/287, 292, 293, 297, 298, 299, 300, 301; 248/121, 146, 148, 311.2, 359

[56] References Cited

U.S. PATENT DOCUMENTS

| 949,644 | 2/1910 | Borgmeyer | 215/6 |
| 2,706,702 | 4/1955 | Carski | 435/296 X |
| 3,589,983 | 6/1971 | Holderith et al. | 435/296 |
| 3,920,140 | 11/1975 | Kiser | 248/359 X |
| 4,076,592 | 2/1978 | Bradley | 435/33 |
| 4,121,976 | 10/1978 | Gleeson | 435/296 X |
| 4,239,853 | 12/1980 | Bradley | 435/33 |

FOREIGN PATENT DOCUMENTS

| 2754830 | 6/1979 | Fed. Rep. of Germany . |
| 2316327 | 1/1977 | France . |
| 2468643 | 5/1981 | France . |

Primary Examiner—Robert J. Warden
Assistant Examiner—Randall E. Deck
Attorney, Agent, or Firm—Renner, Otto, Boisselle & Lyon

[57] ABSTRACT

A one piece, biphasic media culture container, as disclosed herein, includes a first compartment for a solid nutrient culture medium, a second compartment for a liquid nutrient culture medium and a common headspace enclosure above and extending between said first and second compartments to provide selective fluid communication therebetween. The first and second compartments are discrete from one another except for the common headspace enclosure and are spatially separated by an air space between their respective inner walls.

3 Claims, 4 Drawing Figures

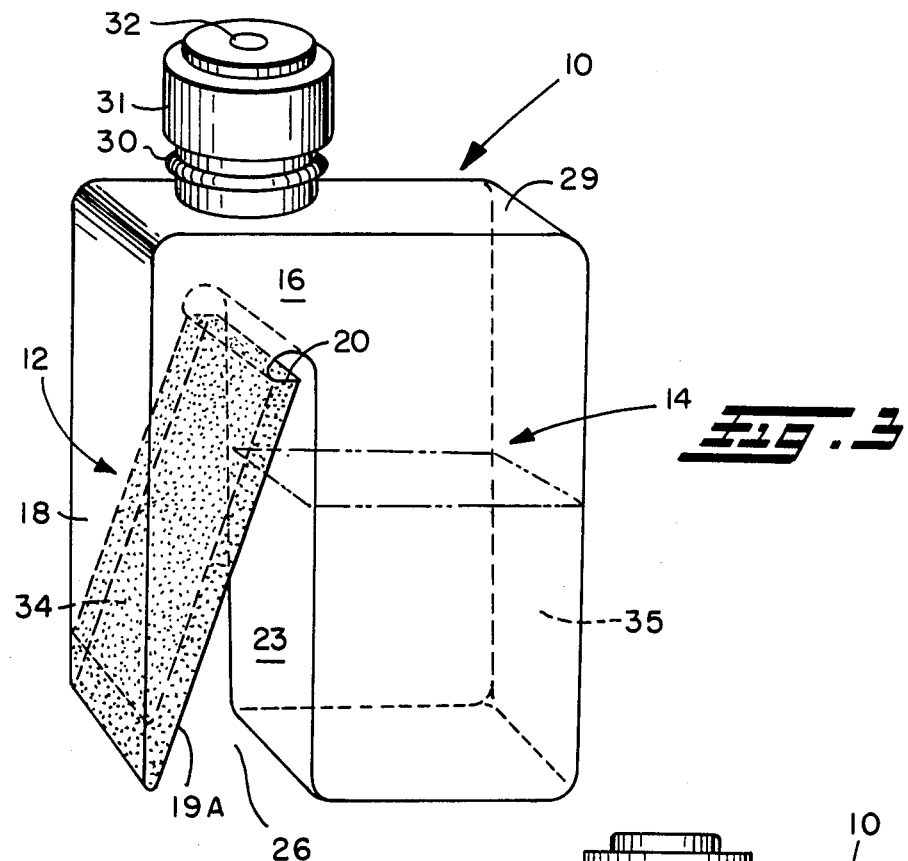
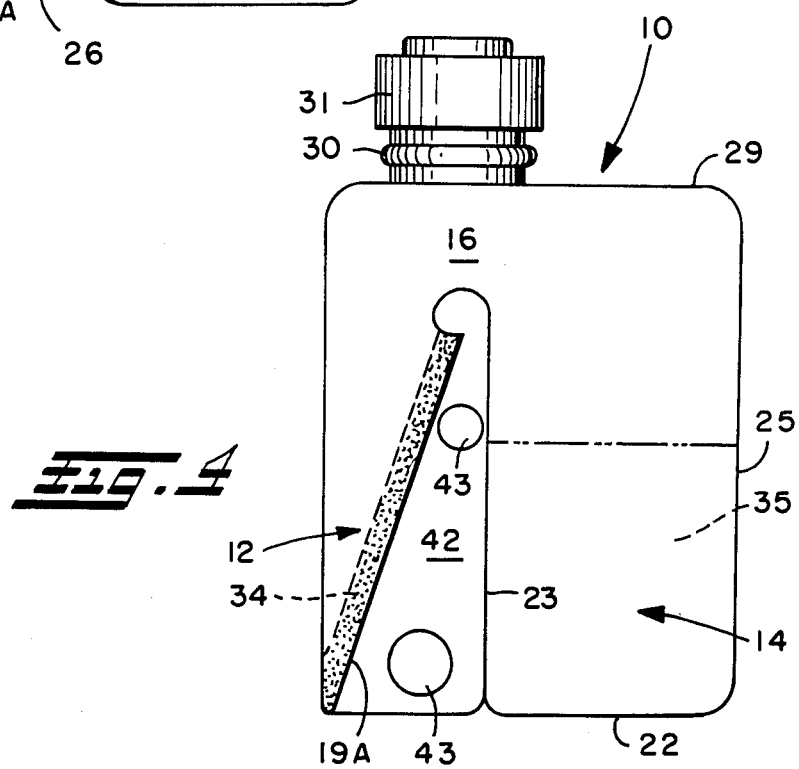

BIPHASIC MEDIA CULTURE APPARATUS

BACKGROUND OF THE INVENTION

This invention relates to culturing of microbial, mammalian, and plant cells, and more specifically to biphasic media culture apparatus for simultaneous inoculation and culture of cells in media having differing compositions and particularly having differing physical characteristics.

In laboratory practice, it is well known in procedures for the detection and identification of infecting organisms, for example, to initially culture a specimen or sample by inoculation into a liquid nutrient medium or broth, and subsequently sub-culture from the liquid medium to a solid nutrient medium in order to isolate individual colonies of a particular organism. The isolated organisms can then be identified or further cultured.

Most commonly, the liquid medium is contained in a tube or bottle, and the solid medium, which generally has an agar base and is introduced warm or hot as a liquid and gels to a solid on cooling to the temperature at which it will be used, is separately contained in a petri dish or plate. The sub-culture from the liquid medium must be aseptically transferred to a separate dish or plate containing the solid medium. Having both the liquid and solid media in a single container allows for proliferation of infecting organisms in the liquid medium, thus simplifying their detection, and then, by washing the broth over the solid medium, subculturing for isolation can be effected without aseptic transfers being necessary.

Culture bottles or flasks containing both liquid and solid media generally comprise a sealed container including the two different nutrient materials, with the solid medium in the form of an agar slant, and so disposed that it may be positioned out of contact with the liquid medium during the incubation period. Bottles of known design, for example, have included indentations along one or more side edges parallel to one face to retain the solid medium in suitable thickness along said face, or, similarly, cleats or ribs around which the medium can solidify may be fashioned into the face to grip the solidified medium.

Culture bottles of this type are subject to several burdensome and costly manufacturing operations since they must be filled in separate aseptic filling operations. Terminal sterilization would melt the agar which could then not be repositioned and resolidified separate from the liquid. Even if the two phases of media are aseptically filled separately, the solid phase must usually be incubated in an inverted position over the liquid to keep it out of contact with the liquid. Under these conditions, even with the application of previously cited mechanical restraints, the agar may be susceptible to pulling away from the retaining structure.

DESCRIPTION OF THE PRIOR ART

Various efforts have been made to overcome the problems inherent in the structures heretofore described, some of which apply to uses other than culturing of cells, in which it is necessary to keep a solid phase medium separate from a liquid likewise maintained therein.

Gleeson U.S. Pat. No. 4,121,976 discloses a culture bottle comprising a plurality of contiguous side and end walls, a base on which the bottle can stand, and a partition wall within the bottle extending generally vertically when the bottle is standing on the base, and generally parallel with one of the end walls. When the bottle is repositioned so as to be supported on said end wall, the partition defines a generally horizontal dish capable of retaining a solid culture medium out of contact with the liquid medium also in the bottle. While this bottle satisfies the requirements for separating the two phases of media, and allows for terminal sterilization of the media, the construction is such that it must be fabricated in two parts which must be welded together to form a closed container. The technical problems in obtaining a weld which will reliably provide a hermetic seal between the two parts affects both the economy and functionality of its use.

Holderith U.S. Pat. No. 3,589,983 discloses a biphasic culture bottle or flask having a neck defining a relatively wide opening at one end, and a tray member designed to be inserted into the bottle through the neck opening. The tray member includes an end mating section to frictionally engage the interior wall of the neck thereby securing the tray in the bottle at a location along the center line of such bottle. Solid medium in the tray is kept separate from the liquid medium by positioning the bottle on its side, and in this position the contents may be terminally sterilized. Because the solid medium must be filled while warm and in a liquid state, either the medium must be filled into the tray first and allowed to gel before insertion of the tray into the bottle, or the medium must be introduced while the bottle is positioned on its side. The structural configuration of the tray member to allow for securing by frictional engagement with the neck makes filling after the tray has been inserted into the flask both a difficult and time-consuming operation. Prior filling of the tray is similarly time-consuming and costly. The bottle must be positioned on its side and maintained in such position during sterilization and cooling until the agar has set.

Another culture device, disclosed in Fink U.S. Pat. No. 3,563,859, utilizes a culture media support contained in an independent container for incubation and colony growth. In this construction, an insert device has recesses formed on its surface for containing solid culture media, and guide rails formed on opposing sides of the insert which cooperate with guide slots within the container to hold the insert in a fixed position inside the container. The insert is so formed that liquid medium or sample contained within the enclosure will drip down out of contact with the solid medium. This construction could probably be adapted to biphasic use, but such adaptation would be relatively costly and time-consuming.

Other structural forms have been taught for maintaining different compositions or materials separated from one another in an enclosed container by the use of various partitions. For example, Rodiger U.S. Pat. No. 649,864 discloses a paste-cup or mucilage holder comprising a selectively covered cup having a partition wall formed integrally with the walls of the cup and arranged within and to one side of the center of the cup to form a paste chamber and a brush chamber therein. A similar partition wall is disclosed in Potter U.S. Pat. No. 1,060,023. Schmitt U.S. Pat. No. 941,278 provides a partition to separate paste from water by supporting an auxiliary water receptacle within the larger paste container. While these patented constructions represent means for separating two distinct substances contained therein, they do not relate in any way to separating culturing media and would not be effective for the maintenance of conditions effective for the desired culturing operations.

SUMMARY OF THE INVENTION

The principal object of the present invention is to provide a biphasic media culture apparatus or container providing ease of fabrication as a unitary, one piece structure and providing operational effectiveness and reliability.

Another object of the present invention is to provide a biphasic media culture container having discrete and spatially separated first and second compartments sharing common head space in the container. The first compartment receives the liquified solid nutrient medium and the second compartment receives the liquid nutrient media. The air space between the two discrete compartments eliminates the need for a solid internal partition within the container as disclosed in Gleeson U.S. Pat. No. 4,121,976.

BRIEF DESCRIPTION OF THE DRAWINGS

FIG. 3 is a perspective view of an alternative embodiment of the biphasic media culture container of the present invention, wherein the solid nutrient medium compartment of the container has a different configuration.

FIG. 4 is a side view of the alternative embodiment of FIG. 3, showing additional modifications including an exposed handling web extending between the discrete and otherwise spatially separated compartments.

DETAILED DESCRIPTION OF THE PREFERRED EMBODIMENTS

Figure 1:
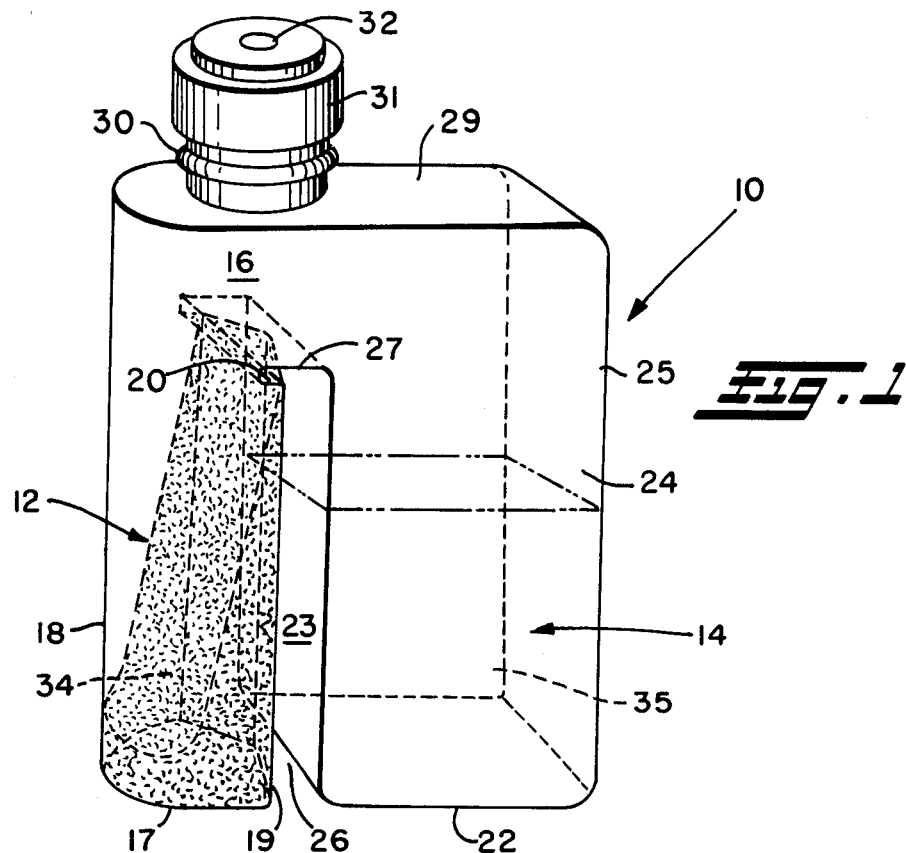
FIG. 1 is a perspective view of one embodiment of the biphasic media culture container of the present invention, showing the relative disposition of the two media received in the two discrete compartments of the container or apparatus when the container is in an upright position.
Figure 2:
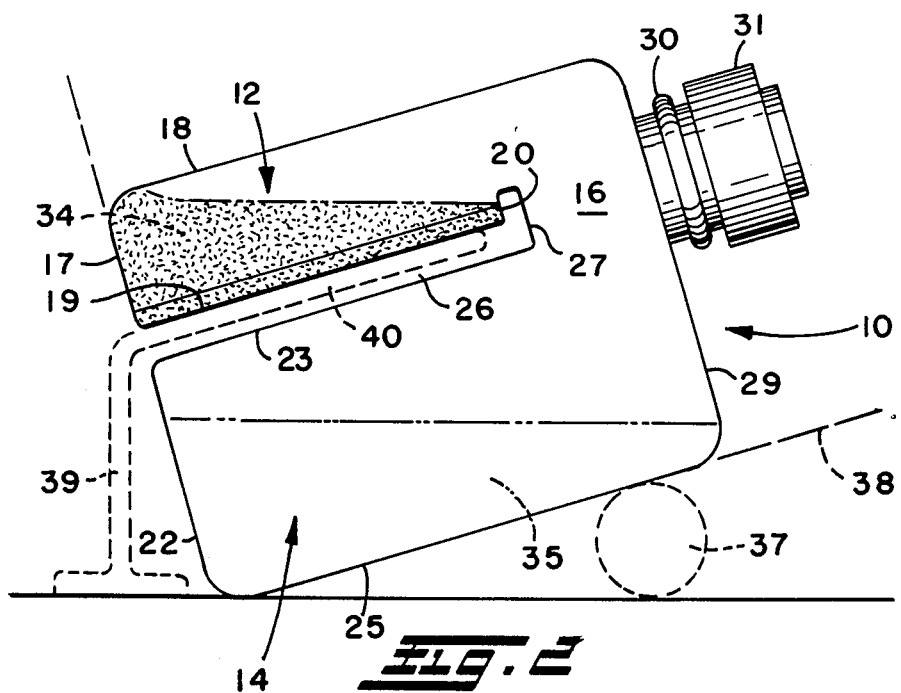
FIG. 2 is a side view of the embodiment of FIG. 1 with the container being tilted to allow the solid phase medium to cool and solidify in a desired slant configuration.

With reference to the drawings and initially to FIGS. 1 and 2, a culture apparatus or container, indicated generally at 10, is made as an integral, unitary body from a suitable, transparent material, such as high melting point thermoplastic polymers or glass. The one-piece container 10 includes a first compartment 12 and a second compartment 14, discrete and spatially separated from each other with respect to their bases and side walls, but sharing a common enclosed headspace 16.

The first compartment 14 is defined by a base 17, an outer arcuate sidewall 18 and a V-shape inner wall 19. The upper end of inner wall 19 terminates in shoulder 20 extending into the first compartment 12, which shoulder is generally perpendicular to inner wall 19 and parallel to base 17. The shape or configuration of the sidewall and/or inner wall of the first compartment may encompass many different profiles according to the application. The volume of the first compartment 12 is preferably about one-quarter to one-half of the volume of the second compartment 14.

The second compartment 14 is defined by a base 22, an inner wall 23, two parallel sidewalls 24 and an end wall 25. The base 22 is preferably coplanar with base 17 cumulatively to provide a relatively large base area for supporting the container 10 in the upright position of FIG. 1. The respective inner walls 19 and 23 are spatially separated from one another and define a recess 26 therebetween extending from an open end between the respective bases to a blind end formed by bridge wall 27 extending between the two compartments and defining thereabove the common headspace enclosure 16.

The common headspace 16 is enclosed by side and end walls integrally formed with the respective walls of the two compartments and by a top wall 29. The common headspace 16 provides selective fluid communication between chambers 12 and 14.

The container top 29 has an opening therein and a threaded neck 30 extending upwardly therefrom. The neck defines an access orifice positioned to span both compartments to allow direct communication therethrough with either compartment, said neck being hermetically sealable by means of a screw cap 31, or other tightly securable closure. The cap 31 has a puncturable but self resealing septum 32, to permit liquid specimens to be introduced into the container without requiring aseptic removal of the cap.

In normal practice, the container compartments are initially filled to appropriate levels through the open top orifice, with the container being in its vertical or upstanding position of FIG. 1. To this end, an appropriate volume of a liquified solid nutrient medium 34, such as an agar or other gel material composition, at a temperature above its gel point, is introduced into the first compartment 12, and a similarly appropriate volume of a liquid nutrient medium 35 is introduced into the second compartment, usually with the container in the vertical position of FIG. 1 with the neck disposed vertically. The apparatus or container 10 is then sealed with cap 31 and may be heat sterilized, such as by autoclaving under suitable time and temperature conditions, while maintained in a vertical position.

Following sterilization, but before the contents cool to the gelling temperature of the solid phase medium 34, the container is tilted to an angle such that the medium in the first compartment 12 assumes the shape that will be recognized by those skilled in the art as a "slant" or "slope", as illustrated in FIG. 2. The volume of medium 34 and the container angle are selected so that a portion of the solid medium 34 beyond the actual slant surface 19 extends past base 17 to contact the arcuate side wall 18. This contact with the base 17 and side wall 18 helps to physically secure the medium 34 in the compartment 12. The shoulder 20 acts as a restraint or dam to the medium 34 to retain the same in compartment 12 during the gelling process.

Holding the container in its tilted attitude may be achieved, for example, by resting the end wall 25 of the liquid medium compartment against a suitable support 37, by placing the entire apparatus in a suitably formed rack positioned to hold the apparatus at the desired angle as denoted by broken lines 38, and/or by utilizing a support stand 39. The support stand 39 includes a suitably angled arm 40 slidably received in the recess 26 between the two compartments 12 and 14. It can be appreciated that heat sterilization could also be carried out with the apparatus in this tilted position without compromising the medium in either of the compartments, thereby eliminating the need for repositioning the container or containers before cooling.

After the solid phase medium has gelled, the specimen for culturing, such as a blood sample (or other microbial, mammalian or plant cell sample), may be inserted or inoculated into the liquid medium 35 by injection through septum 32. Subsequently the liquid medium in the second compartment may be washed back and forth over the solid medium in the first compartment by inversion and similar manipulation of the container. The enclosed common headspace 16 provides the fluid communication necessary for this selectively performed washing action.

FIG. 3 illustrates an alternative configuration of the container 10, modified primarily in the shape and structure of the first, or solid medium compartment 12. In this configuration, the inner wall 19A of the first compartment is flat and angled away from the second compartment from top to bottom. The solid phase medium solidifies as a flat slab or layer because of the flat inner wall 19A, thereby reducing the volume of medium required to obtain a desired surface area, and reducing the possibility of spill-over while the medium is in a liquid state.

In FIG. 4, the container 10 has the same general configuration as the container in FIG. 3, but shows a further modification. In molding the container of FIG. 4, a connecting member or web 42 of approximately the same thickness as the walls of the compartments, has been added to extend between the respective inner walls 19A and 23 of the two compartments 12 and 14. This web should preferably be positioned at or close to a plane through the center of the container 10. Circular holes 43 may be provided in the web to allow horizontal passage of one or more rods, bars or similar supports therethrough to controllably move and reposition one or several appropriately racked containers of the present invention into a desired position for sterilization or for cooling and solidification of the solid phase medium. Similarly disposed in suitable racks for incubation, several containers can be manipulated simultaneously to wash the liquid medium over the solid medium and return the liquid to its own compartment.

It will be apparent from the foregoing that changes may be made in the details of construction and configuration without departing from the spirit of the invention as defined in the following claims.

I claim:

1. An apparatus for culturing microbial, mammalian, and plant cells comprising a one piece container made from a transparent material and having only two compartments formed by respective base means and wall means wherein the base and wall means of the first compartment includes a first base and first inner wall and the base and wall means of the second compartment includes a second base coplanar with and spaced from the first base and a second inner wall spaced from the first inner wall to define a recess therebetween, the first compartment for liquifiable but normally solid nutrient medium and the second compartment for liquid nutrient medium, said compartments being separated by the recess and being discrete from each other with respect to their respective base means and wall means but sharing a common headspace extending between said first and second compartments to provide selective fluid communication therebetween, said headspace being enclosed by a top wall having a neck extending upwardly from said top wall to define a sealable access orifice therein positioned selectively to provide direct communication with either compartment, said neck being closed and hermetically sealed with a screw cap having a puncturable but self resealing septum therein to permit sample injection for culturing without breaking the hermetic seal between the cap and the neck and a connecting member of material extending between the opposing inner walls of the respective compartments across the recess therebetween, said connecting member being configured to allow the container to be conveniently tilted to permit the solid nutrient medium to gel on a slant in the first compartment and to be conveniently inverted or agitated to wash the liquid medium back and forth over the solid medium.

2. The apparatus of claim 1 wherein the inner wall of the first compartment has a flat surface extending angularly away from the second compartment from top to bottom and has an upper end terminating in a shoulder projecting into the first compartment.

3. An apparatus for culturing microbial, mammalian, and plant cells comprising a one piece container having only two compartments made from a transparent material and formed by respective base means and wall means wherein the base and wall means of the first compartment includes a first base and a first inner wall and the base and wall means of the second compartment includes a second base coplanar with and spaced from the first base and a second inner wall spaced from the first inner wall to define a recess therebetween, the first compartment for liquifiable but normally solid nutrient medium and the second compartment for liquid nutrient medium, said compartments being separated by the recess and being discrete from each other with respect to their respective base means and wall means but sharing a common headspace extending between said first and second compartments to provide selective fluid communication therebetween, said headspace being enclosed by a top wall having a neck extending upwardly from said top wall to define a sealable access orifice therein positioned selectively to provide direct communication with either compartment, said neck being closed and hermetically sealed by a screw cap having a puncturable but self resealing septum therein to permit sample injection for culturing without breaking the hermetic seal between the cap and the neck and a support means including an angled arm selectively slidably received in the recess between compartments selectively to hold the container in a tilted position to permit the solid nutrient medium to gel on a slant after being inserted into the first compartment in its liquid phase.

* * * * *